United States Patent [19]

Miller

[11] Patent Number: 4,551,438

[45] Date of Patent: Nov. 5, 1985

[54] OLIGOMERIZATION OF LIQUID OLEFIN OVER A NICKEL-CONTAINING SILICACEOUS CRYSTALLINE MOLECULAR SIEVE AND HYDROCARBYL ALUMINUM HALIDE

[75] Inventor: Stephen J. Miller, San Francisco, Calif.

[73] Assignee: Chevron Research Company, San Francisco, Calif.

[21] Appl. No.: 598,772

[22] Filed: Apr. 11, 1984

[51] Int. Cl.$^4$ .............................................. B01J 29/28
[52] U.S. Cl. ...................................... 502/62; 502/66; 502/67; 502/71
[58] Field of Search ............................ 502/62, 66, 71; 585/255, 533

[56] References Cited

U.S. PATENT DOCUMENTS

| | | | |
|---|---|---|---|
| 3,244,768 | 4/1966 | Holt | 502/62 X |
| 4,017,553 | 4/1977 | Cesca et al. | 585/255 X |
| 4,417,088 | 11/1983 | Miller | 585/533 |
| 4,446,243 | 5/1984 | Chester et al. | 502/62 |

FOREIGN PATENT DOCUMENTS

2000508 7/1971 Fed. Rep. of Germany ........ 502/62

*Primary Examiner*—Carl F. Dees
*Attorney, Agent, or Firm*—S. R. LaPaglia; W. K. Turner; V. J. Cavalieri

[57] ABSTRACT

A process for oligomerizing olefins in the liquid phase using a catalyst composition comprising a nickel-containing silicaceous crystalline molecular sieve catalyst and an hydrocarbyl-aluminum halide.

15 Claims, 1 Drawing Figure

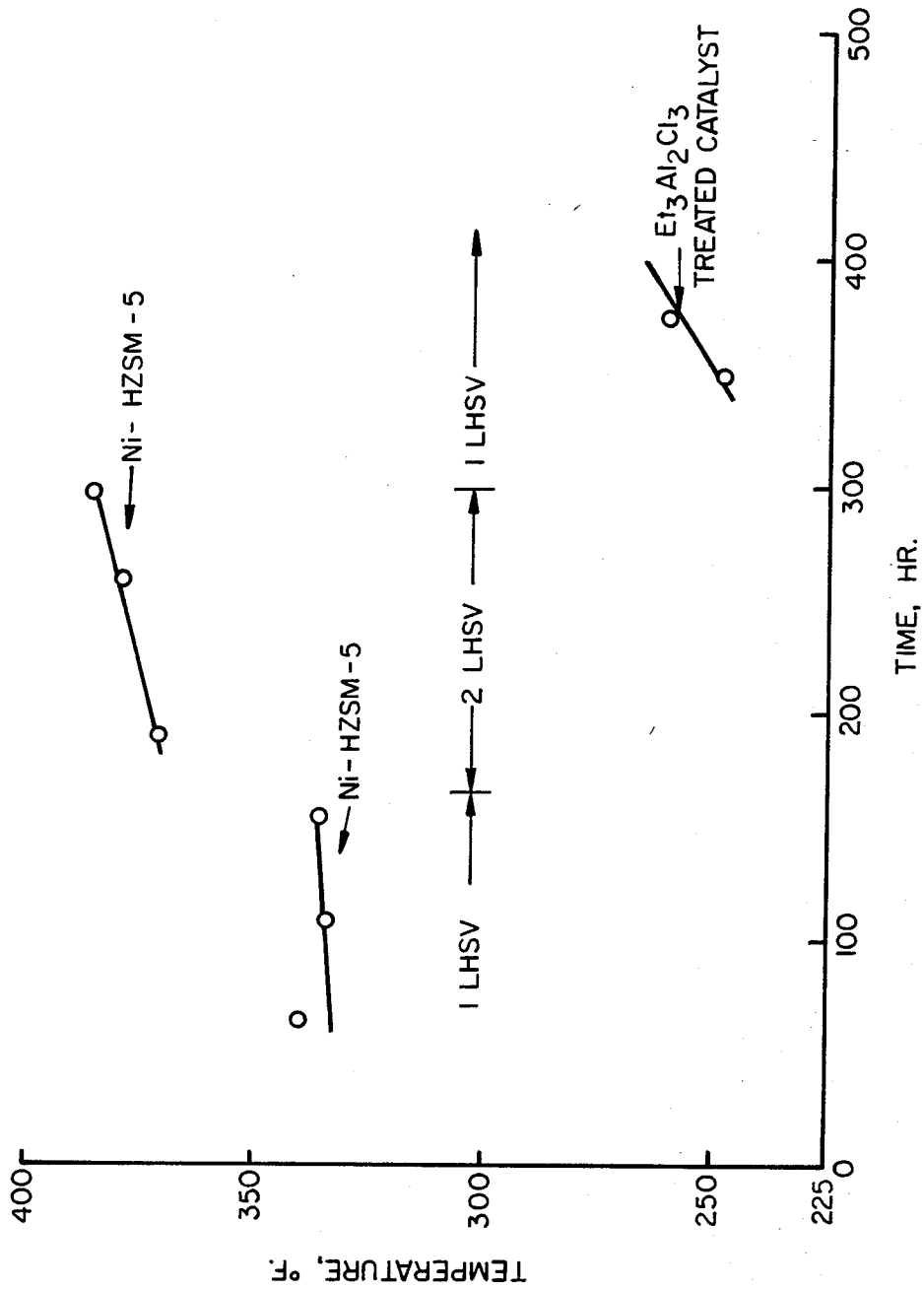

OLIGOMERIZATION OF LIQUID OLEFIN OVER A NICKEL-CONTAINING SILICACEOUS CRYSTALLINE MOLECULAR SIEVE AND HYDROCARBYL ALUMINUM HALIDE

BACKGROUND OF THE INVENTION

1. Field of Invention

The present invention is in the field of olefin oligomerization. More specifically, the present invention relates to oligomerization of olefins in the liquid phase with a catalyst comprising the combination of a nickel-containing silicaceous crystalline molecular sieve and a hydrocarbyl aluminum halide.

2. Description of the Prior Art

Non-zeolitic catalyst combinations using hydrocarbyl aluminum halides for oligomerizing olefins are known in the art. For example, U.S. Pat. Nos. 4,366,083 and 4,283,305 disclose catalyst compositions for oligomerizing olefins obtained by contacting a hydrocarbyl aluminum halide and a nickel carboxylate.

U.S. Pat. No. 3,622,469 discloses a catalyst system comprising $NiCl_2$, triisopropylphosphine and an hydrocarbyl aluminum halide to convert propylene to a mixture of $C_6$ olefins.

Oligomerization and polymerization of olefins in the gas phase over various zeolites is also known in the art. For example, U.S. Pat. No. 3,960,978 a process for producing a gasoline fraction containing predominantly olefinic compounds which comprises contacting a $C_2$ to $C_5$ olefin with a ZSM-5 type crystalline aluminosilicate zeolite at a temperature of from about 500° F. to about 900° F. is disclosed.

U.S. Pat. No. 4,021,502 describes the conversion of gaseous $C_2$ to $C_5$ olefins into gasoline blending stock by passage over ZSM-12 at temperatures of from about 400° F. to about 1200° F.

U.S. Pat. No. 4,254,295 discloses a process for the oligomerization of olefins by contacting said olefins in the liquid phase with ZSM-12 catalyst at temperatures of 80° F. to 400° F.

In copending application U.S. Ser. Nos. 584,031 and 584,078, both filed on Feb. 27, 1984, of common inventive entity processes are disclosed for oligomerizing $C_2$–$C_{20}$ olefins by contacting said olefins in the liquid phase with a nickel-containing silicaceous crystalline molecular sieve catalyst.

It has now been found that the activity of the nickel-containing silicaceous crystalline molecular sieve catalyst described in the above-mentioned co-pending applications, for oligomerizing $C_2$ to $C_{20}$ olefins may be increased by combining the catalysts with a hydrocarbyl aluminum halide.

SUMMARY OF THE INVENTION

The present invention provides a catalyst composition especially suited for promoting oligomerization of $C_2$ to $C_{20}$ olefins comprising at least one hydrocarbyl aluminum halide and at least one nickel-containing silicaceous crystalline molecular sieve in the hydrogen form selected from the group consisting of ZSM-5, ZSM-11, crystalline admixtures of ZSM-5 and ZSM-11, silicalite, organosilicate disclosed in Ser. No. Re 29,948 and CZM or mixtures thereof; the molar ratio of the hydrocarbyl aluminum halide to the nickel being from 1:1 to 10:1 and preferably 1:1 to 4:1.

The present invention also provides a process for oligomerizing alkenes by contacting $C_2$ to $C_{20}$ olefins or mixtures thereof in the liquid phase with a catalytically effective amount of such a catalyst composition, at a temperature of from about 45° F. to about 450° F. and pressure conditions which are suitable for promoting a polymerization reaction and for maintaining the reactants in the liquid phase.

It has been found that the present process provides selective conversion of the olefin feed to oligomer products. The present process effects the conversion of the olefin feed to dimer, trimer, tetramer, etc., products with high selectivity. The product of the present reaction thus contains primarily olefin oligomer and little or no light cracked products, paraffins, etc.

The high selectivity is in part due to the surprisingly high oligomerization activity of the catalyst of the present process, which permits high conversion at low temperatures where cracking reactions are minimized.

The oligomers which are the products of the process of this invention are medium to heavy olefins which are highly useful for both fuels and chemicals. These include olefinic gasoline, such as from propylene dimerization, and extremely high quality midbarrel fuels, such as jet fuel. Higher molecular weight compounds can be used without further reaction as components of functional fluids such as lubricants, as viscosity index improvers in lubricants, as hydraulic fluids, as transmission fluids, and as insulating oils, e.g., in transformers to replace PCB containing oils. These olefins can also undergo chemical reactions to produce surfactants which in turn can be used as additives to improve the operating characteristics of the compositions to which they are added (e.g., lubricating oils) or can be used as primary surfactants in highly important activities such as enhanced oil recovery or as detergents. Among the most used surfactants prepared from the heavy olefins are alkyl sulfonates and alkyl aryl sulfonates.

A significant feature of the present process is the liquid phase contacting of the olefin feed only the combination of a nickel-containing silicaceous crystalline molecular sieve and a hydrocarbyl aluminum halide. There will be appreciated that the pressures and temperatures employed must be sufficient to maintain the system in the liquid phase. As is known to those in the art, the pressure will be a function of the number of carbon atoms of the feed olefin and the temperature.

The oligomerization process described herein may be carried out as a batch type, semi-continuous or continuous operation utilizing a fixed or moving bed catalyst system.

BRIEF DESCRIPTION OF THE DRAWING

FIG. 1 is a graph showing a plot of temperature for 70% conversion of $C_6$–$C_9$ gasoline feed to higher boiling product versus time over Ni-HZSM-5 and triethyl-trichlorodialuminum treated Ni-HZSM-5 catalyst.

DESCRIPTION OF SPECIFIC EMBODIMENTS

The feeds used in the process of the invention contain alkenes which are liquids under the conditions in the oligomerization reaction zone. Under standard operating procedures it is normal both to know the chemical composition of feedstocks being introduced into a reaction zone and to set and control the temperature and pressure in the reaction zone. Once the chemical composition of a feedstock is known, the temperature and hydrocarbon partial pressures which will maintain all or part of the feed as liquids can be determined using standard tables or routine calculations. Conversely, once the desired temperature and pressure to be used in the reaction zone are set, it becomes a matter of routine to determine what feeds and feed components would or would not be liquids in the reactor. These calculations involve using critical temperatures and pressures. Critical temperatures and pressures for pure organic compounds can be found in standard reference works such as *CRC Handbook of Chemistry and Physics, International Critical Tables, Handbook of Tables for Applied Engineering Science,* and Kudchaker, Alani, and Zwolinski, Chemical Reviews 68, 659 (1968), all of which are incorporated herein by reference. The critical temperature for a pure compound is that temperature above which the compound cannot be liquefied regardless of pressure. The critical pressure is the vapor pressure of the pure compound at its critical temperature. These points for several pure alkenes are listed below:

|  | $T_c$ °C. | (°F.) | $P_c$-atm (bar) |
|---|---|---|---|
| ethene | 9.21 | (48.6) | 49.66 (50.3) |
| propene | 91.8 | (197.2) | 45.6 (46.2) |
| 1-butene | 146.4 | (295.5) | 39.7 (40.2) |
| 1-pentene | 191.59 | (376.9) | 40 (40.5) |
| iso-2-pentene | 203 | (397) | 36 (36.5) |
| 1-hexene | 230.83 | (447.49) | 30.8 (31.2) |
| 1-heptene | 264.08 | (507.34) | 27.8 (28.2) |
| 1-octene | 293.4 | (560.1) | 25.6 (25.9) |
| 1-decene | 342 | (648) | 22.4 (22.7) |

It can be appreciated that at temperatures above about 205° C. (401° F.), pure $C_5$ and lower alkenes must be gaseous, while pure $C_6$ and higher alkenes can still be liquefied by applying pressure. Similarly, above about 275° C. (527° F.) pure $C_8$ and higher alkenes can be maintained in the liquid state, while pure $C_7$ and lower alkenes must be gaseous.

Typical feeds are mixtures of compounds. But even so, once the chemical composition of the feed is known, the critical temperature and pressure of the mixture can be determined from the ratios of the chemicals and the critical points of the pure compounds. See for example, the methods of Kay and Edmister in *Perry's Chemical Engineers Handbook,* 4th Edition, pages 3–214, 3–215 (McGraw Hill, 1963), which is incorporated by reference.

Of course, the only constraint on the alkenes present in the feed and which are to react in the oligomerization reaction zone is that these alkenes be liquids under the conditions in the reaction zone (the conditions include a temperature of less than about 450° F.). The chemical composition of the alkenes can be varied to obtain any desired reaction mixture or product mix, so long as at least some of the alkene components of the feed are liquid.

The alkene chains can be branched. And, even though the nickel-containing silicaceous crystalline molecular sieve catalysts used in this invention are intermediate pore size molecular sieves, alkenes having quaternary carbons (two branches on the same carbon atom) can be used. But where quaternary carbons are present, it is preferred that the branches are methyl.

The preferred alkenes are straight chain, or n-alkenes, and the preferred n-alkenes and 1-alkenes. The alkenes have from 2 to 20 carbon atoms, and more preferably have from about 2 to about 6 carbon atoms.

One of the surprising discoveries of this invention is that under certain reaction conditions, longer chain alkenes can be polymerized instead of being cracked to short chain compounds. Additionally, the oligomers produced from long n-1-alkenes are very highly desirable for use as lubricants. The oligomers have surprisingly little branching so they have very high viscosity indices, yet they have enough branching to have very low pour points.

The feed alkenes can be prepared from any source by standard methods. Sources of such olefins can include FCC offgas, coker offgas, syngas (by use of CO reduction catalysts), low pressure, nonhydrogenative zeolite dewaxing, alkanols (using high silica zeolites), and dewaxing with crystalline silica polymorphs. Highly suitable n-1-alkene feeds, especially for preparing lubricating oil base stocks, can be obtained by thermal cracking of hydrocarbonaceous compositions which contain normal paraffins or by Ziegler polymerization of ethene.

Often, suitable feeds are prepared from lower alkenes which themselves are polymerized. Such feeds include polymer gasoline from bulk $H_3PO_4$ polymerization, and propylene dimer, and other olefinic polymers in the $C_4$–$C_{20}$ range prepared by processes known to the art.

The nickel-containing silicaceous crystalline molecular sieves used in this invention are of intermediate pore size. By "intermediate pore size", as used herein, is meant an effective pore aperture in the range of about 5 to 6.5 Angstroms when the molecular sieve is in the H-form. Molecular sieves having pore apertures in this range tend to have unique molecular sieving characteristics. Unlike small pore zeolites such as erionite and chabazite, they will allow hydrocarbons having some branching into the molecular sieve void spaces. Unlike larger pore zeolites such as the faujasites and mordenites, they can differentiate between n-alkanes and slightly branched alkanes on the one hand and larger branched alkanes having, for example, quaternary carbon atoms.

The effective pore size of the molecular sieves can be measured using standard adsorption techniques and hydrocarbonaceous compounds of known minimum kinetic diameters. See Breck, *Zeolite Molecular Sieves,* 1974 (especially Chapter 8) and Anderson et al, *J. Catalysis* 58, 114 (1979), both of which are incorporated by reference.

Intermediate pore size molecular sieves in the H-form will typically admit molecules having kinetic diameters of 5.0 to 6.5 Angstroms with little hindrance. Examples of such compounds (and their kinetic diameters in Angstroms) are: n-hexane (4.3), 3-methylpentane (5.5), benzene (5.85), and toluene (5.8). Compound having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), m-xylene (6.1), and 1,2,3,4-tetramethylbenzene (6.4). Generally, compounds having kinetic diameters of greater than about 6.5 Angstroms do not penetrate the pore apertures and thus are not absorbed into the interior of the molecular sieve lattice. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms.

In performing adsorption measurements to determine pore size, standard techniques are used. It is convenient to consider a particular molecule as excluded if it does not reach at least 95% of its equilibrium adsorption value on the zeolite in less than about 10 minutes ($p/p_o=0.5$; 25° C.).

Nickel-containing HZSM-5 is described in U.S. Pat. Nos. 3,702,886 and 3,770,614.

HZSM-11 is described in U.S. Pat. No. 3,709,979, "Crystalline admixtures" of ZSM-5 and ZSM-11 also exist, which are thought to be the result of faults occurring within the crystal or crystallite area during the synthesis of the zeolites. The "Crystalline admixtures" are themselves zeolites but have characteristics in common, in a uniform or nonuniform manner, to what the literature reports as distinct zeolites. Examples of crystalline admixtures of ZSM-5 and ZSM-11 are disclosed and claimed in U.S. Pat. No. 4,229,424, Kokotailo, Oct. 21, 1980 (incorporated by reference). The crystalline admixtures are themselves intermediate pore size zeolites and are not to be confused with physical admixtures of zeolites in which distinct crystals or crystallites of different zeolites are physically present in the same catalyst composite or hydrothermal reaction mixture.

Silicalite is disclosed in U.S. Pat. No. 4,061,724; the "RE 29,948 organosilicates" are disclosed in Ser. No. Re. 29,948; chromia silicates, CZM, are disclosed in Ser. No. 450,419, Miller, filed Dec. 16, 1982. These patents are incorporated herein by reference.

The crystalline silica polymorphs, silicalite, and Ser. No. Re. 29,948 organosilicates, and the chromia silicate, CZM are essentially alumina free.

"Essentially alumina free", as used herein, is meant the product silica polymorph (or essentially alumina-free silicaceous crystalline molecular sieve) has a silica:alumina mole ratio of greater than 200:1, preferably greater than 500:1. The term "essentially alumina free" is used because it is difficult to prepare completely aluminum free reaction mixtures for synthesizing these materials. Especially when commercial silica sources are used, aluminum is almost always present to a greater or lesser degree. The hydrothermal reaction mixtures from which the essentially alumina free crystalline silicaceous molecular sieves are prepared can also be referred to as being substantially aluminum free. By this usage is meant that no aluminum is intentionally added to the reaction mixture, e.g., as an alumina or aluminate reagent, and that to the extent aluminum is present, it occurs only as a contaminant in the reagents.

Of course, these and the other molecular sieves can be used in physical admixtures.

When synthesized in the alkali metal form, the zeolites may be conveniently converted to the hydrogen form by well known ion exchange reactions, for example, by intermediate formation of the ammonium form as a result of ammonium ion exchange and calcination of the ammonium form to yield the hydrogen form or by treatment with dilute acid such as hydrochloric acid.

Nickel is incorporated into these silicaceous crystalline molecular sieves according to techniques well known in the art such as impregnation and cation exchange. For example, typical ion exchange techniques would be to contact the particular sieve in the hydrogen form with an aqueous solution of a nickel salt. Although a wide variety of salts can be employed, particular preference is given to chlorides, nitrates and sulfates. The amount of nickel in the zeolites range from 0.5% to 10% by weight and preferably from 1% to 5% by weight.

Representative ion exchange techniques are disclosed in a wide variety of patents including U.S. Pat. Nos. 3,140,249; 3,140,251; 3,960,978, 3,140,253 and 4,061,724.

Following contact with the salt solution, the zeolites are preferably washed with water and dried at a temperature ranging from 150° F. to about 500° F. and thereafter heated in air at temperatures ranging from about 500° F. to 1000° F. for periods of time ranging from 1 to 48 hours or more.

The nickel-containing silicaceous crystalline molecular sieve catalysts can be made substantially more stable for oligomerization by including from about 0.2% to 3% by weight and preferably 0.5% to 2% by weight of the Group IIB metals, zinc or cadmium and preferably zinc. A primary characteristic of these substituents is that they are weak bases, and are not easily reduced. These metals can be incorporated into the catalysts using standard impregnation, ion exchange, etc., techniques. Strongly basic metals such as the alkali metals are unsatisfactory as they poison substantially all of the polymerization sites on the zeolite. For this reason, the alkali metal content of the zeolite is less than 1%, preferably less than 0.1%, and most preferably less than 0.01%. The feed should be low in water, i.e., less than 100 ppm, more preferably less than 10 ppm, in sulfur, i.e., less than 100 ppm and preferably less than 10 ppm, in diolefins, i.e., less than 0.5%, preferably less than 0.05% and most preferably less than 0.01%, and especially in nitrogen, i.e., less than 5 ppm, preferably less than 1 ppm and most preferably less than 0.2 ppm.

The polymerization processes of the present invention are surprisingly more efficient with small crystallite sieve particles than with larger crystalline particles. Preferably, the molecular sieve crystals or crystallites are less than about 10 microns, more preferably less than about 1 micron, and most preferably less than about 0.1 micron in the largest dimension. Methods for making molecular sieve crystals in different physical size ranges are known to the art.

The molecular sieves can be composited with inorganic matrix materials, or they can be used with an organic binder. It is preferred to use an inorganic matrix since the molecular sieves, because of their large internal pore volumes, tend to be fragile, and to be subject to physical collapse and attrition during normal loading and unloading of the reaction zones as well as during the oligomerization processes. Where an inorganic matrix is used, it is highly preferred that the matrix be substantially free of hydrocarbon conversion activity. It can be appreciated that if an inorganic matrix having hydrogen transfer activity is used, a significant portion of the oligomers which are produced by the molecular sieve may be converted to paraffins and aromatics and to a large degree the benefits of my invention will be lost.

Preferred hydrocarbyl aluminum halides have the general formula $Al_zR_xY_y$ where R is a hydrocarbon group containing up to 12 carbon atoms, or more, such as alkyl, aryl, aralkyl, alkaryl, cycloalkyl; Y represents halogen: fluorine, chlorine, bromine or iodine; z is 1 or 2, x and y have each a value of 1, 2, 3 or 4 with $(x+y)/z=3$. Examples of such compounds are ethyl aluminum sesquichloride, dichloroethylaluminum, dichloroisobutyl aluminum, chlorodiethylaluminum, tribromotriethyldialuminum, triiodotriethyldialuminum, or their mixtures. Examples of catalyst compositions consist of any one or mixtures of the nickel-containing silicaceous crystalline molecular sieves and any one of the aluminum compounds mentioned above. The preferred hydrocarbyl aluminum halide has the formula $Al_2R_xY_y$, wherein R is alkyl of 1 to 12 carbon atoms, Y is chlorine, x is 2 or 3 and y is 6—x.

The catalyst compositions are produced by intimately contacting the hydrocarbyl aluminum halide and the nickel-containing silicaceous crystalline molecular sieve by conventional contacting techniques, as by contacting a solution of the hydrocarbyl aluminum halide in an inert hydrocarbon solvent, e.g., inert hydrocarbons such as pentane, hexane or benzene for a time sufficient to allow interaction between the hydrocarbyl aluminum halide and the nickel-containing sieve. The contacting may be done in situ in the reactor system by passing the solvent containing the hydrocarbyl aluminum halide through a fixed bed of the nickel-containing catalyst or the two components may be contacted prior to their addition to the reactor or the solvent containing the hydrocarbylaluminum halide may be added to the feed. The contacting is preferably effected before feed addition and in an inert reaction environment, that is, one essentially free from reactive materials such as water and oxygen.

The molar ratio of the hydrocarbyl aluminum halide to the nickel ranges from about 1:1 to 10:1 and preferably from about 1:1 to 4:1.

The precise nature of the interaction between the nickel-containing silicaceous crystalline molecular sieve and the hydrocarbyl aluminum halide is not entirely understood, but it is believed that bridged complexes are formed of the type

wherein X is R or Y as defined hereinabove.

The activity of the nickel-containing silicaceous crystalline molecular sieve catalyst for olefin oligomerization is greatly increased by the addition of the hydrocarbyl aluminum halide. It is believed that the hydrocarbyl aluminum halide acting as a Lewis acid can remove charge from the Ni, thereby increasing its affinity for olefins and, consequently, the reaction rate.

The reaction conditions under which the oligomerization reactions take place include hydrocarbon partial pressures sufficient to maintain the desired alkene reactants in the liquid state in the reaction zone. Of course, the larger the alkene molecules, the lower the pressure required to maintain the liquid state at a given temperature. As described above, the operating pressure is intimately related to the chemical composition of the feed, but can be readily determined. Thus, the required hydrocarbon partial pressure can range from 31 bar at 450° F. for a pure n-1-hexane feed to about atmospheric pressure for a n-1-$C_{15}$-$C_{20}$ alkene mixture. In the process of this invention, both reactant and product are liquids under the conditions in the reaction zone, thus leading to a relatively high residence time of each molecule in the catalyst.

The reaction zone is typically operated below about 450° F. Above that temperature not only significant cracking of reactants and loss of oligomer product take place, but also significant hydrogen transfer reactions causing loss of olefinic oligomers to paraffins and aromatics take place. An oligomerization temperature in the range from about 90° F. to 350° F. is preferred.

Liquid hourly space velocities can range from 0.05 to 20, preferably from 0.1 to about 4.

Once the effluent from the oligomerization reaction zone is recovered, a number of further processing steps can be performed.

If it is desired to use the long chain compounds which have been formed in middle distillate fuel such as jet or diesel or in lube oils as base stock, the alkene oligomers are preferably hydrogenated.

All or part of the effluent can be contacted with the molecular sieve catalyst in further reaction zones to further react unreacted alkenes and alkene oligomers with themselves and each other to form still longer chain materials. Of course, the longer the carbon chain, the more susceptible the compound is to being cracked. Therefore, where successive oligomerization zones are used, the conditions in each zone must not be so severe as to crack the oligomers. Operating with oligomerization zones in series can also make process control of the exothermic oligomerization reactions much easier.

One particularly desirable method of operation is to separate unreacted alkenes present in the effluent from the alkene oligomers present in the effluent and then to recycle the unreacted alkenes back into the feed.

The following examples further illustrate this invention.

EXAMPLES

Example 1

HZSM-5 zeolite of 80 $SiO_2/Al_2O_3$ mole ratio was mixed with peptized Catapal alumina at a 50/50 sieve/alumina weight ratio, extruded through a 1/16" die, dried overnight at 300° F. under $N_2$, then calcined in air for 8 hours at 850° F. The catalyst was exchanged five times with a 1% aqueous ammonium acetate solution, then washed with water to give a final Na level of 100 ppm.

Example 2

The catalyst of Example 1 was exchanged with a 1% aqueous nickel acetate solution at 180° F. for five hours, washed with water, then dried and calcined as in Example 1. The Ni content of the calcined catalyst was 3 wt %.

Example 3

The catalyst of Example 2 (Ni-HZSM-5) was tested for conversion of an olefinic $C_6$-$C_9$ gasoline feed (Table 1) to higher boiling product. The catalyst temperature was adjusted to maintain 70% conversion as a function of time on stream at 800 psig and at 1 or 2 LHSV, as is shown in FIG. 1.

TABLE 1

| Inspections of $C_6$-$C_9$ Olefinic Gasoline | |
|---|---|
| Gravity, °API | 69.8 |
| Research Octane Number, Clear | 95.5 |
| D-86 Distillation, LV %, °F. | |
| 10/20 | 152/156 |
| 30/50 | 158/162 |
| 70/90 | 190/348 |
| Paraffins, LV % | 0 |
| Olefins, LV % | 99 |
| Naphthenes, LV % | 0 |
| Aromatics, LV % | 1 |

Example 4

After the catalyst in Example 3 has run for 300 hours, the feed was stopped and the catalyst (4 grams) treated in situ at 300° F. with 50 cc of a 6 wt % solution of $Et_3Al_2Cl_3$ in hexane at 6 cc/hr. Excess reagent was removed with hexane and the catalyst stripped for one hour with $N_2$. Upon starting the olefinic feed, activity increased approximately 80° F. versus what it had been prior to the alkyl aluminum halide addition (FIG. 1).

Example 5

Five (5) grams of the catalyst of Example 2 were treated in situ at 300° F. with 1.2 g $Et_3Al_2Cl_3$ dissolved in hexane. Excess reagent was washed off with hexane, and the catalyst stripped with $N_2$. Propylene was then fed in at 90° F., 1 LHSV, and 800 psig. At 120 hours on-stream, conversion to $C_5+$ was 95 wt. %. Product inspections (propylene dimer distribution) are shown in Table II.

TABLE II

| $C_6$ Olefin Composition From Propylene Oligomerization | |
| --- | --- |
| $C_6$ Olefin Selectivity | % |
| 4-m-2-$C_5$= | 49.5 |
| 3-, 4-m-1-$C_5$= | 1.7 |
| 2-m-2-$C_5$= | 18.2 |
| 2-m-1-$C_5$= | 2.9 |
| 3-m-2-$C_5$= | 0 |
| n-$C_6$= | 23.8 |
| 2,3-dm-$C_4$= | 3.9 |

What is claimed is:

1. A catalyst composition for promoting oligomerization of olefins, said composition comprising the components:
   (a) a nickel-containing silicaceous crystalline molecular sieve in the hydrogen form selected from the group consisting of ZSM-5, ZSM-11, crystalline admixtures of ZSM-5 and ZSM-11, silicalite, an organic silicate disclosed in Ser. No. Re. 29,948 and CZM or mixtures thereof; and
   (b) at least one hydrocarbyl aluminum halide; the molar ratio of the hydrocarbyl aluminum halide to the nickel being from 1:1 to 10:1.

2. The catalyst composition of claim 1 wherein the nickel-containing silicaceous crystalline molecular sieve also contains zinc cation.

3. The catalyst composition of claim 1 wherein said nickel-containing silicaceous crystalline molecular sieve is silicalite.

4. The catalyst composition of claim 1 wherein said nickel-containing silicaceous crystalline molecular sieve is organosilicate disclosed in Ser. No. Re. 29,948.

5. The catalyst composition of claim 1 wherein said nickel-containing silicaceous crystalline molecular sieve is CZM.

6. The catalyst composition of claim 1 wherein said nickel-containing silicaceous crystalline molecular sieve is ZSM-5.

7. The catalyst composition of claim 1 wherein said nickel-containing silicaceous crystalline molecular sieve is ZSM-11.

8. The catalyst composition of claim 1 wherein said nickel-containing silicaceous crystalline molecular sieve is a crystalline or physical admixture of ZSM-5 and ZSM-11.

9. The catalyst composition of claim 1 wherein the hydrocarbyl aluminum halide has the formula $Al_zR_zY_y$, wherein R is $C_{1-12}$ hydrocarbyl; Y is halogen; z is 1 or 2, x and y are each 1, 2, 3 or 4; and $(x+y)/z=3$.

10. The catalyst composition of claim 9 wherein R is $C_{1-12}$ alkyl; Y is chlorine; x is 3; and y is 3.

11. The catalyst composition of claim 9 wherein R is $C_{1-12}$ alkyl; Y is chlorine; x is 2; and y is 4.

12. The catalyst composition of claim 9 wherein the hydrocarbyl aluminum halide has the formula $Al_2R_xY_y$; wherein R is $C_{1-12}$ alkyl; Y is chlorine; x is 2 or 3; and y is 6-x.

13. The catalyst composition of claim 12 wherein the hydrocarbyl aluminum halide has the formula $Al_2R_xY_y$; wherein R is $C_{1-12}$ alkyl; Y is chlorine; x is 2; and y is 4.

14. The catalyst composition of claim 9 wherein the hydrocarbyl aluminum halide is ethyl aluminum sesquichloride, dichloroethylaluminum, dichloroisobutylaluminum, chlorodiethylaluminum, chlorodiisobutylaluminum, tribromotriethyldialuminum, triiodotriethylalumium or mixtures thereof.

15. The catalyst compound of claim 9 wherein the hydrocarbyl aluminum halide is trichlorotriethyldialuminum.

* * * * *

UNITED STATES PATENT AND TRADEMARK OFFICE
CERTIFICATE OF CORRECTION

PATENT NO. : 4,551,438
DATED : November 5, 1985
INVENTOR(S) : Stephen J. Miller

It is certified that error appears in the above-identified patent and that said Letters Patent is hereby corrected as shown below:

Column 3, line 63, "and 1-alkenes" -- are 1-alkenes --.

Column 10, line 24, "$Al_z R_z Y_y$" should read -- $Al_z R_x Y_y$ --.

Signed and Sealed this

Tenth Day of June 1986

[SEAL]

Attest:

DONALD J. QUIGG

Attesting Officer

Commissioner of Patents and Trademarks